US012669817B2

(12) United States Patent
Cabibihan et al.

(10) Patent No.: US 12,669,817 B2
(45) Date of Patent: Jun. 30, 2026

(54) TELEPRESENCE CONTROL SCHEMES FOR HAZARDOUS ENVIRONMENTS

(71) Applicant: Qatar Foundation for Education, Science and Community Development, Doha (QA)

(72) Inventors: John Cabibihan, Doha (QA); Sammy Sedrati, Doha (QA); Mohamed Ali Hammami, Doha (QA)

(73) Assignee: Qatar Foundation for Education, Science and Community Development, Doha (QA)

( * ) Notice: Subject to any disclaimer, the term of this patent is extended or adjusted under 35 U.S.C. 154(b) by 380 days.

(21) Appl. No.: 17/559,007

(22) Filed: Dec. 22, 2021

(65) Prior Publication Data

US 2022/0197277 A1     Jun. 23, 2022

Related U.S. Application Data

(60) Provisional application No. 63/130,004, filed on Dec. 23, 2020.

(51) Int. Cl.
*G05D 1/00* (2024.01)
*A61L 2/10* (2026.01)
(Continued)

(52) U.S. Cl.
CPC .............. *G05D 1/0038* (2013.01); *A61L 2/10* (2013.01); *A61L 2/24* (2013.01); *A61L 9/20* (2013.01);
(Continued)

(58) Field of Classification Search
CPC .. G05D 1/0038; G05D 1/0044; G05D 1/0225; G05D 1/0246; G05D 1/0274; G05D 2201/0203; G05D 1/0016; A61L 2/10; A61L 2/24; A61L 9/20; A61L 2202/14; A61L 2202/16; A61L 2202/25;
(Continued)

(56) References Cited

U.S. PATENT DOCUMENTS 11,272,823 B2 * 3/2022 Orzechowski ....... G05D 1/0274
11,511,423 B2 * 11/2022 Vitzrabin .................. A61L 2/24
(Continued)

OTHER PUBLICATIONS

European Commission "Danish disinfection robots save lives in the fight against the Corona virus", 2010. available at https://digital-strategy.ec.europa.eu/en/news/danish-disinfection-robots-save-lives-fight-against-corona-virus (Year: 2010).*
(Continued)

*Primary Examiner* — Anne Marie Antonucci
*Assistant Examiner* — Misa H Nguyen
(74) *Attorney, Agent, or Firm* — K&L Gates LLP

(57)     ABSTRACT

A system includes a mobile robot, a first imaging device configured to inspect an area surrounding the mobile robot, a UV disinfection mechanism attached to the mobile robot, and a telepresence control mechanism configured to control the mobile robot. The UV disinfection mechanism is configured to disinfect the area surrounding the mobile robot. The telepresence control mechanism is configured to allow a user of the mobile robot to control the mobile robot remotely. The mobile robot has a mapping functionality and a navigation functionality.

13 Claims, 7 Drawing Sheets

(51) Int. Cl.

| | |
|---|---|
| *A61L 2/24* | (2006.01) |
| *A61L 9/20* | (2006.01) |
| *A61L 103/75* | (2026.01) |
| *G06F 3/04817* | (2022.01) |
| *G06F 3/16* | (2006.01) |
| *G06V 40/20* | (2022.01) |

(52) U.S. Cl.
   CPC ......... *G05D 1/0044* (2013.01); *G05D 1/0225* (2013.01); *G05D 1/0246* (2013.01); *G05D 1/0274* (2013.01); *G06F 3/04817* (2013.01); *G06F 3/167* (2013.01); *G06V 40/28* (2022.01); *A61L 2103/75* (2026.01); *A61L 2202/14* (2013.01); *A61L 2202/16* (2013.01); *A61L 2209/111* (2013.01)

(58) Field of Classification Search
   CPC ........... A61L 2209/111; G06F 3/04817; G06F 3/167; G06F 3/011; G06F 3/017; G06V 40/28
   See application file for complete search history.

(56) References Cited

U.S. PATENT DOCUMENTS

| | | | | |
|---|---|---|---|---|
| 11,580,724 | B2 * | 2/2023 | Ma | G06V 20/20 |
| 11,602,845 | B2 * | 3/2023 | Rubæk | B25J 9/1679 |
| 2012/0197464 | A1 * | 8/2012 | Wang | G05D 1/024 |
| | | | | 701/28 |
| 2017/0185830 | A1 * | 6/2017 | Srivastava | G02B 27/017 |
| 2021/0072536 | A1 * | 3/2021 | Lee | G02B 27/0176 |
| 2021/0124539 | A1 * | 4/2021 | Matysiak | G06F 3/1294 |
| 2021/0135468 | A1 * | 5/2021 | Park | H02J 7/0048 |
| 2021/0233314 | A1 * | 7/2021 | Johnson | G02B 27/0172 |

OTHER PUBLICATIONS

Gordon; CSAIL robot disinfects Greater Boston Food Bank; MIT News; 2020; (7 pages).
Omnilabs; "UV-C Light to Disinfect Spaces"; https://ohmnilabs. com/powerful-disinfection-robot-for-safer-healthier-spaces/? campaignid=567202211&adgroupid=1188573778145055&adid= &hsa_acc=9177033811&hsa_cam=17193099811&hsa_grp= 1188573778145055&hsa_ad=&hsa_src=o&hsa_tgt=kwd- 74286107797526:loc-190&hsa_kw=uv%20light% 20disinfection%.

* cited by examiner

230

220

VR Controllers

210

140

360 Streaming Camera

120

110

GPC Mobile Robot

TELEPRESENCE CONTROL SCHEMES FOR HAZARDOUS ENVIRONMENTS

PRIORITY CLAIM

The present application claims priority to and the benefit of U.S. Provisional Patent Applications No. 63/130,004, filed on Dec. 23, 2020, the entirety of which is incorporated herein by reference.

BACKGROUND

The transmission of SARS-CoV-2, the virus that causes COVID-19, may be worsened by the ability of the virus to survive on surfaces for days after an infected individual was present in the area. The specific proportion of those cases that were acquired through surfaces or through aerosol dispersion in the air may not be known. Research studies investigating the ability of SARS-CoV-2 to survive on various materials have demonstrated that the virus can remain active for up to 2 to 3 days on common surfaces, such as metals, plastic, and cardboard.

As a result, contamination with the virus, as well as its resulting disease COVID-19, can continue to occur for days after an infected person has been present in a given location. Surface disinfection procedures may be therefore necessary to eliminate contamination and reduce the spread of the virus. According to the World Health Organization, sanitation protocols must be performed meticulously at least once per day. Manual cleaning procedures can pose a risk to those performing them. Additionally, performed alone, they are less effective than when combined with automated sanitation protocols.

SUMMARY

The present disclosure provides a semi-autonomous, remotely controlled robotic disinfection system that may combine the dynamic nature of manual cleaning with the meticulousness of an automated system. In an example, a system may include a mobile robot, a first imaging device configured to inspect an area surrounding the mobile robot, a UV disinfection mechanism attached to the mobile robot, and a telepresence control mechanism configured to control the mobile robot. The UV disinfection mechanism may be configured to disinfect the area surrounding the mobile robot. The telepresence control mechanism may be configured to allow a user of the mobile robot to control the mobile robot remotely. The mobile robot may have a mapping functionality and a navigation functionality.

In some examples, the first imaging device of the mobile robot may include a scanner configured to provide the mapping functionality by mapping the area surrounding the mobile robot.

In some examples, the first imaging device of the mobile robot may include a camera configured to provide a 360° view of the area surrounding the mobile robot.

In some examples, based on information from the first imaging device, the mobile robot may be configured to determine a potential target cleaning location.

In some examples, responsive to determining a presence of a person in the area surrounding the mobile robot, the system may be configured to turn off a UV light from the UV disinfection mechanism.

In some examples, the UV disinfection mechanism may include a UV lamp configured to emit a short-wave UV light having a wavelength in a range of 100 nm to 280 nm.

In some examples, the UV disinfection mechanism may be configured to eliminate over 99% of SARS-CoV-2 virus in a disinfected area.

In some examples, the navigation functionality of the mobile robot may be configured to drive the mobile robot autonomously.

In some examples, responsive to determining that a charging state of the mobile robot is lower than a predetermined value, the mobile robot may be configured to autonomously move to a power dock for charging.

In some examples, the telepresence control mechanism may include a user controller configured to transmit a control instruction to the mobile robot remotely.

In some examples, the user controller is configured to detect a user gesture via a second imaging device in the user controller and translate the user gesture into the control instruction.

In some examples, the user controller may be configured to detect a voice command and translate the voice command into the control instruction.

In some examples, the user controller may be configured to provide a virtual control icon to the user, receive a user command through the virtual control icon, and translate the user command into the control instruction.

In some examples, the virtual control icon may include a virtual map including a plurality of predefined target locations, and the control instruction comprises an instruction to move the mobile robot to one of the plurality of predefined target locations.

In some examples, the user controller may be configured to provide a teleportation portal to the user, receive a user command through the teleportation portal, and translate the user command into the control instruction.

In some examples, the teleportation portal may include a predefined target location. The control instruction may include an instruction to move the mobile robot to the target location.

In other examples, a system may include a mobile robot, a first imaging device configured to inspect an area surrounding the mobile robot, a UV disinfection mechanism attached to the mobile robot, and a telepresence control mechanism configured to control the mobile robot. The UV disinfection mechanism may be configured to disinfect the area surrounding the mobile robot. The telepresence control mechanism may include a wearable user controller configured to transmit a control instruction to the mobile robot remotely. The mobile robot may have a mapping functionality and a navigation functionality.

The advantages discussed herein may be found in one, or some, and perhaps not all of the embodiments disclosed herein. Additional features and advantages are described herein, and will be apparent from the following Detailed Description and the figures.

DETAILED DESCRIPTION

As of Oct. 2020, there are around 129,000 Covid-19 cases recorded in Qatar and 39.3 million cases worldwide. The proportion of those cases that were acquired through surfaces or through aerosol dispersion in the air may not be known. However, there is increasing scientific evidence that ultraviolet (UV) light type C can deactivate SARS-CoV-2 virus.

Aspects of the present disclosure may provide a semi-autonomous, remotely controlled robotic disinfection system that combines the dynamic nature of manual cleaning with the meticulousness of an automated system. The system may use ultraviolet light (UV-C) technology. UV-C technology may have a 99.8% kill rate against bacterial and viral strains, and may not have lingering side effects as compared to commonly used chemical disinfectants.

Aspects of the present disclosure may be in the domain of telepresence control. Telepresence may refer to devices or machines that will allow users to work remotely in another room or another location. With telepresence, the user may feel that they are present in another location even if they are not. Further, telepresence control may prevent UV-C light from harming the human eyes and skin by distancing the user from the system when the UV-C light is activated.

UV light disinfection robots may be one of the emerging and successful of robotics. Aspects of the present disclosure may be a semi-automated disinfection approach utilizing robotics and UV light to eliminate surface contamination in public spaces. A telepresence system may be integrated into a working autonomous UV-C robot that may allow a user to navigate potentially hazardous environments. The robotic system may include a mobile robot, the robot's mapping and navigation capability, a UV disinfection system, and a telepresence control system.

With the addition of a telepresence system, a safe method can be achieved for the effective disinfection of public spaces that are otherwise difficult to thoroughly sanitize. By doing so, aspects of the present disclosure may provide a solution to deal with the infectious nature of COVID-19, as well as other transmittable pathogen-borne diseases.

Figure 1:
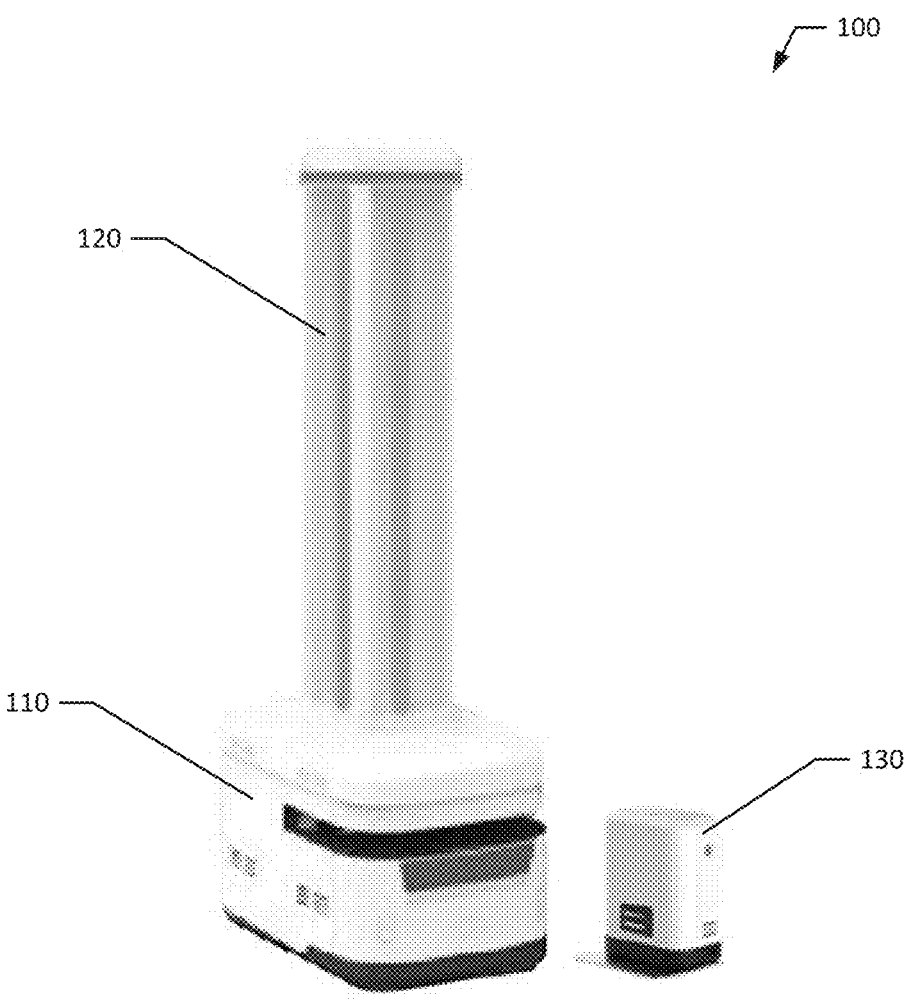
FIG. 1 illustrates an example of a system having a mobile robot, a UV disinfection mechanism, and a charging dock.
Figure 2:
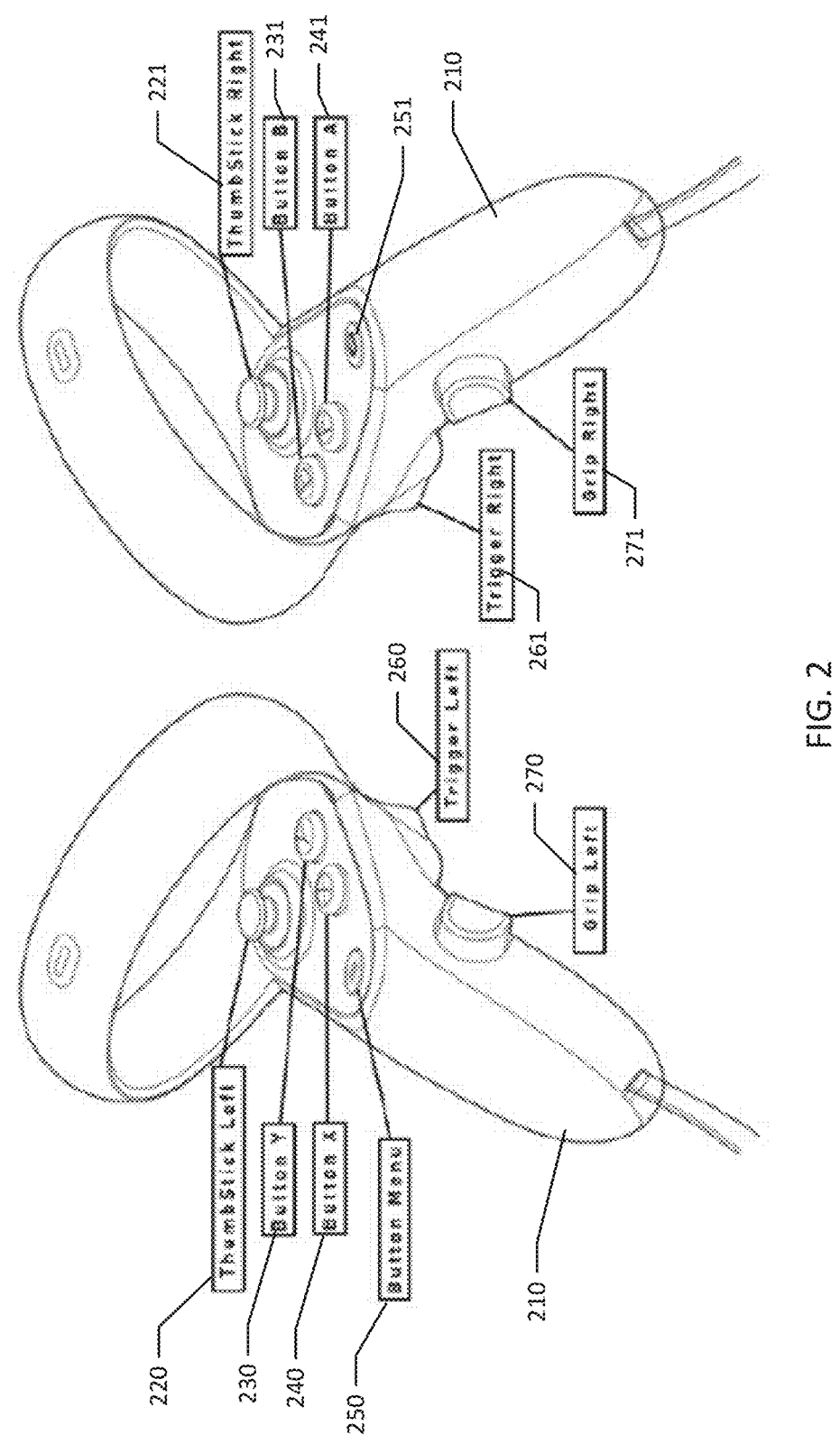
FIG. 2 illustrates an example of a user controller.
Figure 3:
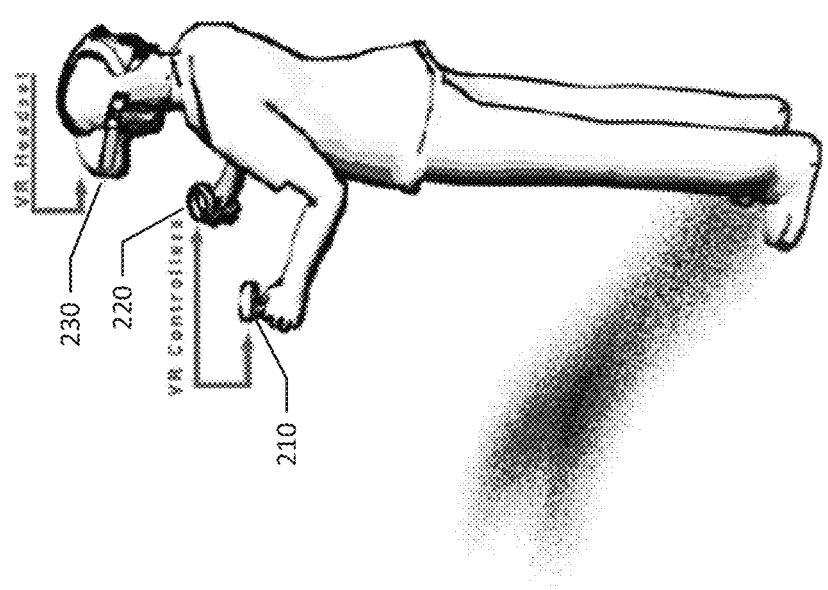
FIG. 3 illustrates an example scenario of a telepresence control of the mobile robot of FIG. 1 using a user controller.
Figure 3:
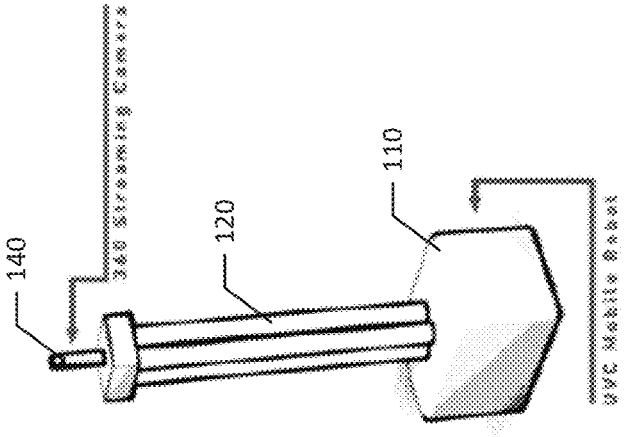

Referring to FIGS. 1 to 3, in some examples, a system 100 according to the present disclosure may include a mobile robot 110 and a UV disinfection system/mechanism 120 attached to the mobile robot 110. The UV disinfection mechanism 120 may be configured to disinfect the area surrounding the mobile robot 110.

In some examples, the mobile robot 110 may be an automated guided vehicle. In some examples, the mobile robot 110 may have a size of 620×440×330 mm³ and a payload of 100 kg, and a speed of 1.2 m/s. In other examples, the mobile robot 110 may have any other suitable size, payload, and speed.

In some examples, the mobile robot 110 may have a mapping functionality and a navigation functionality. In some examples, the system 100 may further include an imaging device configured to inspect an area surrounding the mobile robot 110. In some examples, the imaging device of the mobile robot 110 may include a camera 140. The camera 140 may provide a 360° view of the area surrounding the mobile robot 110. In some examples, the camera 140 may be disposed on the top surface of the UV disinfection mechanism 120. In other examples, the camera 140 may be disposed in any other suitable location in the system. In some examples, the imaging device may provide the mapping functionality by mapping the area surrounding the mobile robot 110. In some examples, the imaging device of the mobile robot 110 may further include a scanner (e.g., a laser scanner) configured to provide the mapping functionality by mapping the area surrounding the mobile robot 110.

In some examples, based on information from the imaging device, the mobile robot 110 may determine a potential target cleaning location. In some examples, the system 100 (e.g., the mobile robot 110) may determine a presence of a person in the area surrounding the mobile robot 110. Responsive to determining the presence of a person in the area surrounding the mobile robot 110 and/or near the mobile robot 110 (e.g., within a predetermined distance), the system 100 may turn off a UV light from the UV disinfection mechanism 120.

In some examples, the UV disinfection mechanism 120 may include UV lamps configured to emit a UV light. The UV light from the UV lamps may be a short-wave UV light having a wavelength in a range of 100 nm to 280 nm. The UV disinfection mechanism 120 may eliminate over 99% of SARS-CoV-2 virus in an area disinfected by the UV disinfection mechanism 120. For example, with 5 mJ/cm² dose of UV-C light for 6 seconds, it has been found that there was 99% reduction of the SARS-CoV-2 virus.

In some examples, the UV disinfection mechanism 120 may include a low-pressure mercury vapor ultraviolet (UV) type C light source. In some examples, four UV lamps (e.g., Philips, TUV T8) may be installed in the mobile robot 110. In other examples, any other suitable number of UV lamps (e.g., 1, 2, 3, 5, 6, 7, 8, 9, 10, and so on) may be installed in the mobile robot 110. In some examples, the UV lamp may emit short-wave UV radiation with a peak at 253.7 nm in the spectrum of UV type C wavelength. In some examples, the short-wave UV radiation of the the UV lamp may have any other suitable peak value in the spectrum of UV type C wavelength. In some examples, these lamps may be used in industrial water and air disinfection units.

In some examples, the navigation functionality of the mobile robot 110 may allow the mobile robot 110 to be driven autonomously. For example, using the navigation functionality, the mobile robot 110 may be automatically driven according to a preprogramed algorithm.

In some examples, the system 100 may further include a power dock 130. Responsive to determining that a charging state of the mobile robot 110 is lower than a predetermined charging value (e.g., 10%, 20%, or 30%), the mobile robot 110 may autonomously move to the power dock 130 for charging.

In some examples, the system 100 may further include a telepresence control system/mechanism configured to control the mobile robot 110. The telepresence control mechanism may allow a user of the mobile robot to control the mobile robot 110 remotely. In some examples, the telepresence control mechanism may include one or more user controllers 210, 220, and 230. In some examples, as illustrated in FIGS. 2 and 3, the user controllers 210, 220 may be a hand controller, and the user controller 230 may be a virtual reality headset. The one or more user controllers may transmit a control instruction to the mobile robot 110 to control the mobile robot 110 remotely.

In some examples, the telepresence control mechanism may include multiple telepresence modalities. As discussed in detail below, the multiple telepresence modalities/modes may use a virtual reality head-mounted display (e.g., in the controller 230). Each of the multiple telepresence modalities/modes may use different control schemes, which may include the use of (i) the controllers 210, 220; (ii) hand gestures; (iii) voice commands; (iv) virtual icons; and (v) teleportation portals. Each of these telepresence modalities/modes will be discussed in detail below.

The first mode may use the user controllers 210, 220 to control the mobile robot 110. As illustrated in FIG. 2, the user controllers 210, 220 may be a hand controller (e.g., one for the left hand, and the other one for the right hand). Each of the user controllers 210, 220 may include various control switches/buttons. For example, the user controller 210 (e.g., for the left hand) may include a thumbstick 220, button Y 230, button X 240, button menu 250, and trigger 260. Similarly, the user controller 220 (e.g., for the right hand) may include a thumbstick 221, button B 231, button A 241, button menu 251, and trigger 261. The user controllers 210, 220 may receive user commands through these various switches/buttons, generate a control instruction based on the user commands, and transmit the control instruction to the mobile robot 110 to control the mobile robot 110 remotely. Each of the user controllers 210, 220 may also include a grip 270, 271 on the inner side of the user controllers 210, 220 to help the user hold the user controllers 210, 220.

The user commands may be input into the controllers 210, 220 by physically pressing the buttons in the controllers 210, 220 or a combination of multiple buttons to activate commands to operate the mobile robot 110. Examples of such commands may include: Movement (forward/backward); Turn (Left/Right); Increase/Decrease velocity; Turn On/Off the UV lights.

Figure 4:
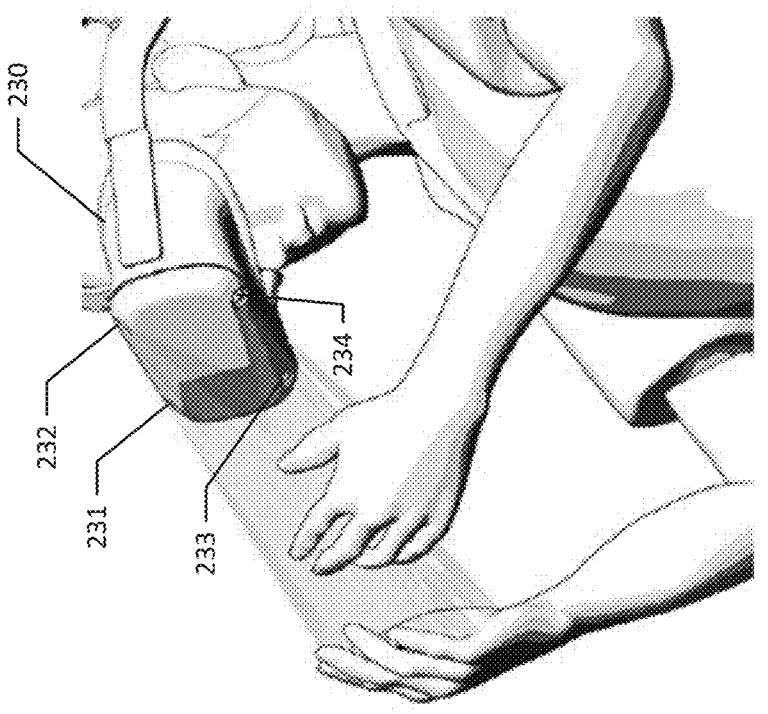
FIG. 4 illustrates an example scenario of a telepresence control of the mobile robot of FIG. 1 using a user gesture.

The second mode may use the user's gestures (e.g., hand gestures). As illustrated in FIG. 4, in some examples, the user controller 230 may detect a user gesture. For example, the user controller 230 may detect the user gesture via one or more imaging devices 231, 232, 233, 234 in the user controller 230 and translate the user gesture into the control instruction to be transmitted to the mobile robot 110. In some examples, the one or more imaging devices 231, 232, 233, 234 may be a camera. The one or more imaging devices 231, 232, 233, 234 of the user controller 230 may detect and scan the surrounding of the user and send a visual feedback to avoid accidental hits and bumps while the user is fully immersed in a virtual world. The one or more imaging devices 231, 232, 233, 234 of the user controller 230 may also track the user's gestures (e.g., user's hands and finger articulations), accurately map the gestures (e.g., hands' bones) to virtual ones, and display a digital replica of them in the virtual world.

Using hand gestures to control the mobile robot 110 and its functions may be achieved by using pre-recorded specific gestures of the hands corresponding to tasks needed to be performed by the robot 110. The action may be performed once the user's gesture (e.g., hand gesture) matches the pre-recorded gesture. Some examples of the gestures may include: Right hand, thumb up: Move forward; Right hand, thumb down: Move backward; Left hand, middle and index fingers extended (V sign): turn on UV lights. This command scheme may not require the usage of the controllers 210, 220, but can complement the controllers 210, 220, for example, in case there is a loss of battery of the controllers 210, 220 during mission critical tasks.

Figure 5:
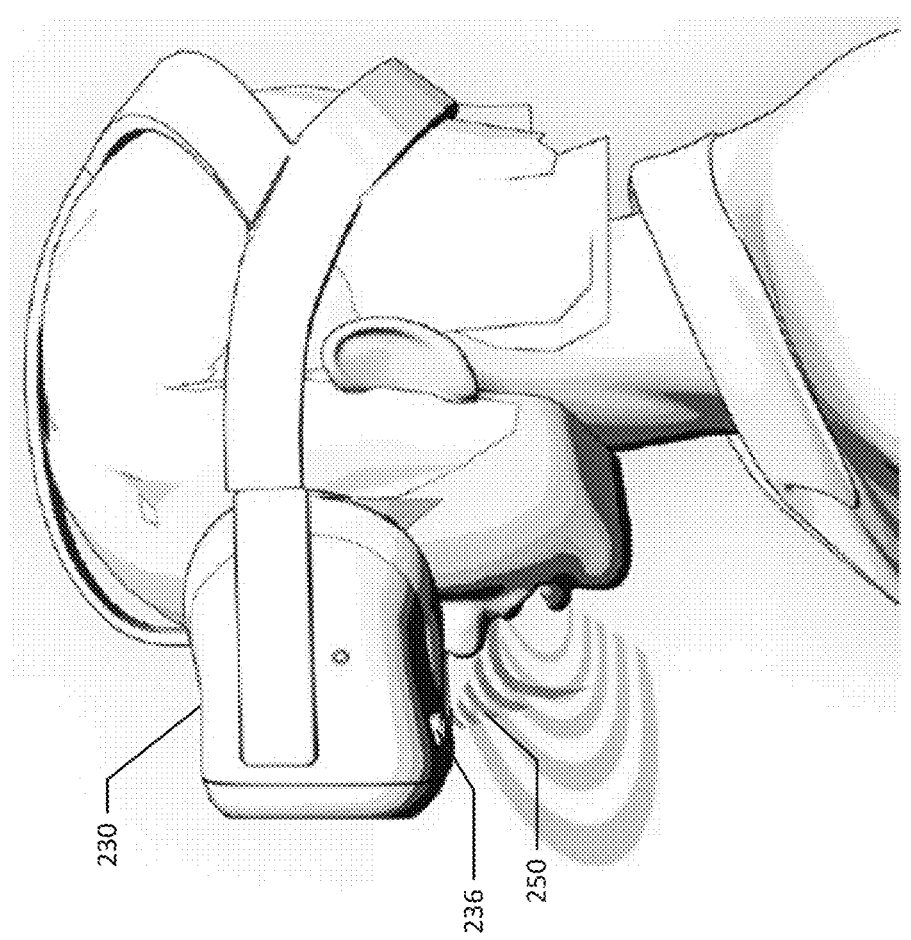
FIG. 5 illustrates an example scenario of a telepresence control of the mobile robot of FIG. 1 using voice commands.

The third mode may use the user's voice commands. In some examples, one or more user controllers 210, 220, 230 may detect a voice command 250 and translate the voice command into the control instruction. For example, as illustrated in FIG. 5, the user controller 230 may detect a voice command 250 and translate the voice command into the control instruction. In some examples, a microphone 236 may be integrated inside the user controller 230. The user's voice command can be used to trigger predefined actions for each vocal command. It is beneficial to have this feature as an alternate to the hand controller 210, 220, for example, in case the hand controller 210, 220 loses battery power. Some examples of the voice/verbal commands may include: Directional commands: "Forward", "Back", "Turn Left", "Turn Right", "Stop"; UV light activation: "Light On", "Light Off."

Figure 6:
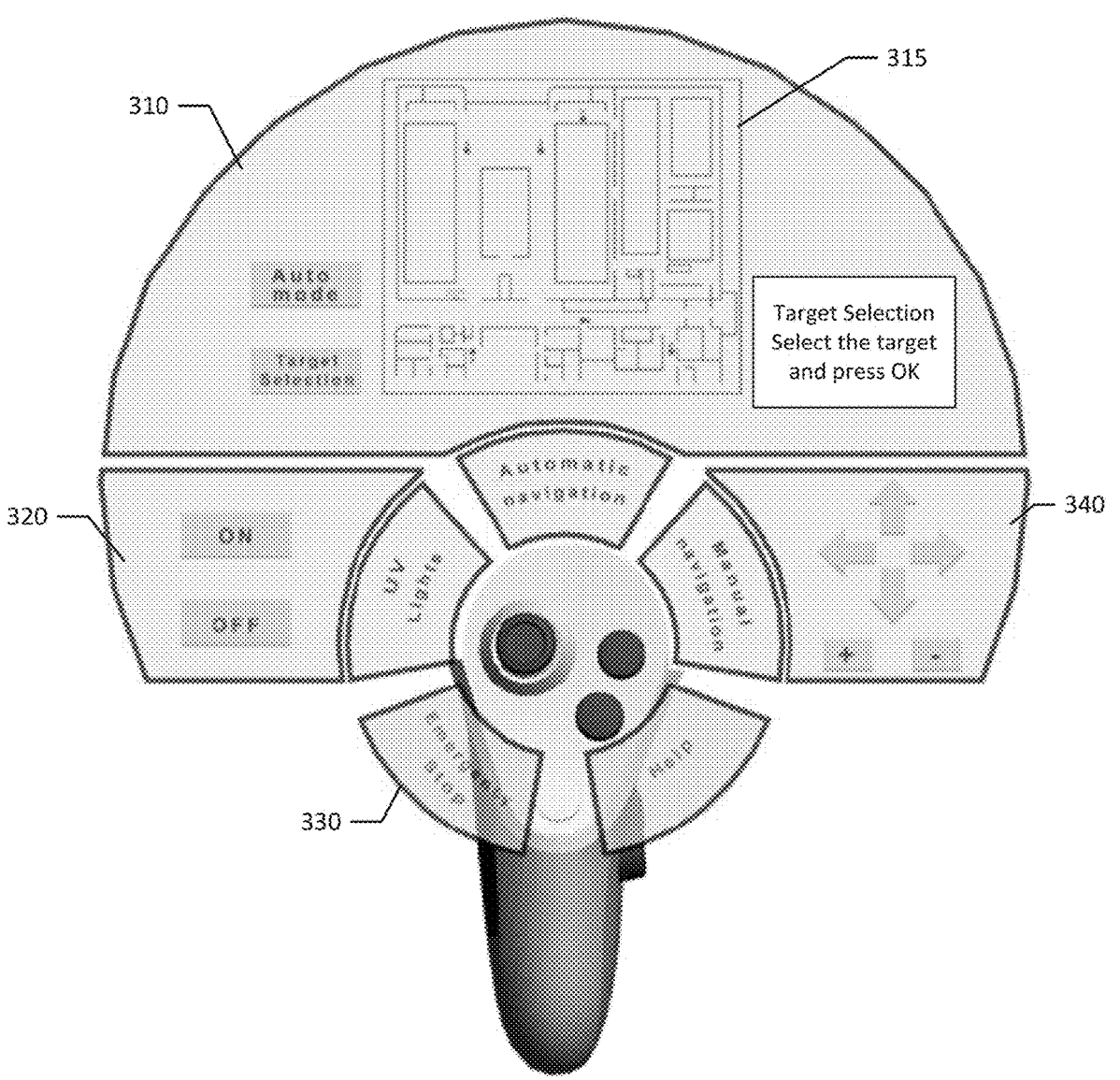
FIG. 6 illustrates an example scenario of a telepresence control of the mobile robot of FIG. 1 using virtual icons.

The fourth mode may include virtual icons. As illustrated in FIG. 6, in some examples, the user controller 230 may provide one or more virtual control icons to the user, for example, through the head-mounted display in the user controller 230. In some examples, the one or more virtual control icons may include four sections. The first virtual section 310 may include an auto mode turn-on button and a target selection button. Next to the target selection button, a virtual map 315 may be provided. The virtual map 315 may be a map showing the area surrounding the mobile robot 110. The virtual map 315 may be generated using the information from the imaging device (scanner and/or camera 140) of the mobile robot 110. With these virtual icons (the target selection button and/or the map 315), the user can select several predefined target locations to move the mobile robot 110 to the selected location.

The second virtual section 320 may include an on/off button, which may turn on/off the mobile robot 110. The third virtual section 330 may include a UV lights button, an automatic navigation button, a manual navigation button, an emergency stop button, and a help button. The UV lights button, when selected, may turn on/off the UV light of the UV disinfection mechanism 120. When the automatic navigation button is selected, the mobile robot 110 may drive in an automatic navigation mode (e.g., according to a random or preprogramed algorithm) without the specific instructions from the user. When the manual navigation button is selected, the mobile robot 110 may drive in a manual navigation mode by receiving specific instructions from the user through the controllers 210, 220, 230. When the emergency stop button is selected, the mobile robot 110 and/or the UV disinfection mechanism 120 may turn off right away. When the help button is selected, the controller 230 may make a call to a local emergency agency (e.g., by dialing 911) or someone who can connect the user to the local emergency agency for an emergency situation.

The fourth virtual section 340 may include direction buttons: forward, backward, left, and right. The mobile robot 110 may move according to the selected direction buttons. The fourth virtual section 340 may further include a plus button and a minus button. These plus/minus buttons may be used to control other parameters of the robot and/or the UV disinfection mechanism 120 (e.g., speed of the robot 110, wavelength of the UV light from the UV disinfection mechanism 120, etc.). In some examples, the virtual icons may appear near the controller 210 or 220 (e.g., on the display of the headset controller 230) as shown in FIG. 6. In other examples, the virtual icons may appear in any other suitable location on the display of the headset controller 230.

In some examples, the system 100 may receive a user command through the one or more virtual control icons, and translate the user command into the control instruction to be transmitted to the mobile robot 110. For example, the control instruction may include an instruction to move the mobile robot to the target location (e.g., the location selected on the map 315). Additional virtual buttons similar to the buttons on the controllers 210, 220, which are described with respect to FIG. 2, can be added to have a larger control with a virtual dashboard.

Figure 7:
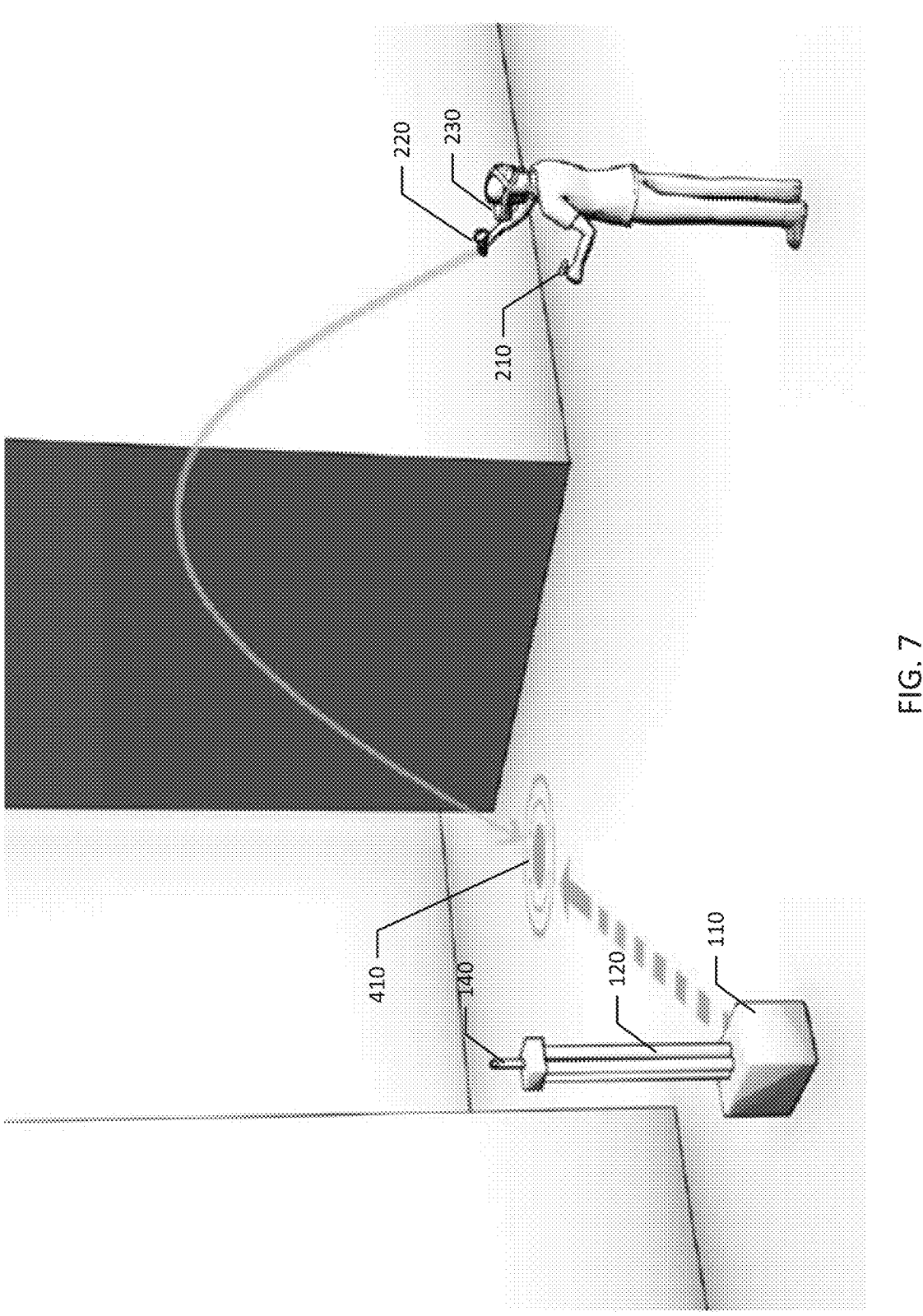
FIG. 7 illustrates an example scenario of a telepresence control of the mobile robot of FIG. 1 using a teleportation portal.

The fifth mode may use a teleportation portal. As illustrated in FIG. 7, in some examples, the user controller 230 may provide teleportation portals to the user. The teleportation portals may be projected in augmented reality. In some examples, the user controller 230 may receive a user command through the teleportation portal, and translate the user command into the control instruction. In some example, the teleportation portal may include a predefined target location. For example, using the teleportation portals, the user may be able to point and select any point (e.g., point 410) in the navigable area within the camera's point of view to move the mobile robot 110 to the selected point. The telepresence control mechanism may project the target destinations on the user's headset (e.g., controller 230) as selectable "teleportation portals" to simplify navigation control. The control instruction may include an instruction to move the mobile robot to the target location. For example, the selection of a target destination may trigger the robot's autonomous navigation system, which may allow the robot 110 to maneuver the environment to reach its destination.

In some examples, the first to third modes may be useful for undefined and detailed locations for navigation. The fourth and fifth modes include predefined locations and, thus, these modes may be useful for deploying the robot 110 in large public spaces, such as in shopping malls.

It will be appreciated that each of the systems, structures, methods and procedures described herein may be implemented using one or more computer program or component. These programs and components may be provided as a series of computer instructions on any conventional computer-readable medium, including random access memory ("RAM"), read only memory ("ROM"), flash memory, magnetic or optical disks, optical memory, or other storage media, and combinations and derivatives thereof. The instructions may be configured to be executed by a processor, which when executing the series of computer instructions performs or facilitates the performance of all or part of the disclosed methods and procedures.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein.

Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above.

The drawing figures are not necessarily to scale. Certain features and components herein may be shown exaggerated in scale or in somewhat schematic form and some details of conventional elements may not be shown in interest of clarity and conciseness.

The terminology used herein is intended to describe particular embodiments only and is not intended to be limiting of the present disclosure. As used herein, the singular forms "a," "an," and "the" are intended to include the plural forms as well, unless otherwise indicated. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the terms "about," "approximately," "substantially," "generally," and the like mean plus or minus 10% of the stated value or range.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Moreover, consistent with current U.S. law, it should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention is claimed as follows:

1. A system comprising:
   a mobile robot;
   a first imaging device configured to inspect an area surrounding the mobile robot;
   a UV disinfection mechanism attached to the mobile robot, wherein the UV disinfection mechanism is configured to disinfect the area surrounding the mobile robot;
   a telepresence control mechanism configured to control the mobile robot, wherein the telepresence control mechanism is configured to allow a user of the mobile robot to control the mobile robot remotely and wherein the telepresence control mechanism comprises a user controller configured to transmit a control instruction to the mobile robot remotely; and
   a second imaging device, wherein the second imaging device is configured to detect and scan the surroundings of the user and send a visual feedback, to avoid accidental contact, to the user,
   wherein the user controller is configured to detect a user gesture via the second imaging device in the user controller and translate the user gesture into the control instruction, wherein the system is further configured to track the user's gestures, map the user's gestures to virtual gestures, and display a digital replica of the user's gestures, wherein the user controller is configured to provide a virtual control icon to the user, receive a user command through the virtual control icon, and translate the user command into the control instruction;

wherein the virtual control icon comprises a virtual map including a plurality of predefined target locations as virtual icons in the virtual map, wherein the control instruction comprises an instruction to move the mobile robot to one of the plurality of predefined target locations;

wherein the mobile robot has a mapping functionality and a navigation functionality; and wherein the user controller is configured to provide a teleportation portal to the user, wherein the teleportation portal allows any point in a navigable area of the mobile robot within a point of view of the first imaging device to be selected, and wherein the user controller is further configured to receive a user command through the teleportation portal, and translate the user command into the control instruction.

2. The system of claim 1, wherein the first imaging device of the mobile robot comprises a scanner configured to provide the mapping functionality by mapping the area surrounding the mobile robot.

3. The system of claim 1, wherein the first imaging device of the mobile robot comprises a camera configured to provide a 360° view of the area surrounding the mobile robot.

4. The system of claim 1, wherein based on information from the first imaging device, the mobile robot is configured to determine a potential target cleaning location.

5. The system of claim 1, wherein responsive to determining a presence of a person in the area surrounding the mobile robot, the system is configured to turn off a UV light from the UV disinfection mechanism.

6. The system of claim 1, wherein the UV disinfection mechanism comprises a UV lamp configured to emit a short-wave UV light having a wavelength in a range of 100 nm to 280 nm.

7. The system of claim 1, wherein the UV disinfection mechanism is configured to eliminate over 99% of SARS-CoV-2 virus in a disinfected area.

8. The system of claim 1, wherein the navigation functionality of the mobile robot is configured to drive the mobile robot autonomously.

9. The system of claim 1, wherein, responsive to determining that a charging state of the mobile robot is lower than a predetermined value, the mobile robot is configured to autonomously move to a power dock for charging.

10. The system of claim 1, wherein the user controller is configured to detect a voice command and translate the voice command into the control instruction.

11. The system of claim 1, wherein the teleportation portal comprises a predefined target location, wherein the control instruction comprises an instruction to move the mobile robot to the target location.

12. A system comprising:

a mobile robot;

a first imaging device configured to inspect an area surrounding the mobile robot;

a UV disinfection mechanism attached to the mobile robot, wherein the UV disinfection mechanism is configured to disinfect the area surrounding the mobile robot;

a telepresence control mechanism configured to control the mobile robot, wherein the telepresence control mechanism comprises a wearable user controller configured to transmit a control instruction to the mobile robot remotely; and a second imaging device, wherein the second imaging device is configured to detect and scan the surroundings of the user and send a visual feedback, to avoid accidental contact, to the user, wherein the wearable user controller is configured to detect a user gesture via the second imaging device in the wearable user controller and translate the user gesture into the control instruction, wherein the system is further configured to track the user's gestures, map the user's gestures to virtual gestures, and display a digital replica of the user's gestures, wherein the user controller is configured to provide a virtual control icon to the user, receive a user command through the virtual control icon, and translate the user command into the control instruction;

wherein the virtual control icon comprises a virtual map including a plurality of predefined target locations as virtual icons in the virtual map, wherein the control instruction comprises an instruction to move the mobile robot to one of the plurality of predefined target locations;

wherein the mobile robot has a mapping functionality and a navigation functionality; and wherein the user controller is configured to provide a teleportation portal to the user, wherein the teleportation portal allows any point in a navigable area of the mobile robot within a point of view of the first imaging device to be selected, and wherein the user controller is further configured to receive a user command through the teleportation portal, and translate the user command into the control instruction.

13. The system of claim 12, wherein the first imaging device of the mobile robot comprises a scanner configured to provide the mapping functionality by mapping the area surrounding the mobile robot.

* * * * *